US007250547B1

(12) United States Patent
Hofmeister et al.

(10) Patent No.: US 7,250,547 B1
(45) Date of Patent: Jul. 31, 2007

(54) WETNESS MONITORING SYSTEM

(75) Inventors: Christopher M. Hofmeister, Menomonee Falls, WI (US); David A. Lange, Milwaukee, WI (US); Charles B. Kendall, Brookfield, WI (US); John G. Schmidt, Lino Lakes, MN (US)

(73) Assignee: RF Technologies, Inc., Brookfield, WI (US)

( * ) Notice: Subject to any disclaimer, the term of this patent is extended or adjusted under 35 U.S.C. 154(b) by 1260 days.

(21) Appl. No.: 09/707,610

(22) Filed: Nov. 7, 2000

(51) Int. Cl.
*A61F 13/15* (2006.01)
*G08B 23/00* (2006.01)
*G08B 21/00* (2006.01)

(52) U.S. Cl. .................. 604/361; 604/362; 340/573.5; 340/604

(58) Field of Classification Search ................ 604/361, 604/362; 340/604, 573.5; 493/383, 334, 493/398
See application file for complete search history.

(56) References Cited

U.S. PATENT DOCUMENTS

| 3,460,123 A | 8/1969 | Bass ........................... 340/235 |
| 3,530,855 A | 9/1970 | Balding ....................... 128/138 |
| 3,759,246 A | 9/1973 | Flack ............................. 128/2 |
| 3,778,570 A | 12/1973 | Shuman ................... 200/61.05 |
| 4,069,817 A | 1/1978 | Fenole ......................... 128/138 |

(Continued)

FOREIGN PATENT DOCUMENTS

JP          57052849          3/1982

(Continued)

OTHER PUBLICATIONS

Article in the Journal of Rehabilitation Research and Development vol. 27 No. 1 Winter 1990 Authors: Pat D. O'Donnell, MD; Cornelia Beck PhD; and Robert C. Walls, PhD.

(Continued)

*Primary Examiner*—Jacqueline F. Stephens
(74) *Attorney, Agent, or Firm*—Jeffrey S. Sokol; Cook & Franke S.C.

(57) ABSTRACT

The present invention relates to a wetness monitoring system that includes a data collection device that sends wetness measurement data to a central computer that detects changes in wetness measurement data caused by the presence of urine or other dielectric fluids. The data collection device includes a semi-reusable sensor and reusable data collector that are worn on a garment of the person. The data collector includes an internal power source so that the person can live a normal ambulatory life. The data collector has an electrical circuit that uses the changing resistance characteristics in the sensor to gather wetness measurement data. The data collector periodically generates and transmits a signal containing the actual wetness measurement data. The signals are coded to identify the particular data collector or person sending the signal. The data collector is programmed to conserve power by sending signals less frequently during periods when the sensor is clearly dry. Signals are sent more frequently when the sensor is damp or a wetness event may have occurred. The central computer receives the signals containing the wetness measurement data and compares the measurement data to an adjustable wetness sensitivity level to determine if a wetness event has occurred. When the central computer determines that a wetness event has occurred, the computer displays the name of the particular person wearing the data collector and the approximate time that the wetness event occurred. The system then pages an appropriate healthcare worker to inform them that the particular individual needs attention and tracks the approximate response times to ensure that the patient is continuously receiving prompt care.

11 Claims, 12 Drawing Sheets

U.S. PATENT DOCUMENTS

| | | | |
|---|---|---|---|
| 4,106,001 A | 8/1978 | Mahoney | 340/604 |
| 4,163,449 A | 8/1979 | Regal | 128/138 |
| 4,191,950 A | 3/1980 | Levin | 340/604 |
| 4,205,672 A | 6/1980 | Dvorak | 128/138 |
| 4,212,295 A | 7/1980 | Snyder | 128/138 |
| 4,356,479 A | 10/1982 | Wilson | 340/604 |
| 4,356,818 A | 11/1982 | Marcias | 128/138 |
| 4,539,559 A | 9/1985 | Kelly et al. | 340/573 |
| 4,640,276 A | 2/1987 | Jing-Sheng | 128/138 |
| 4,653,491 A | 3/1987 | Okada | 128/138 |
| 4,704,108 A | 11/1987 | Okada | 361/604 |
| 4,738,260 A | 4/1988 | Brown | 128/138 |
| 4,754,264 A | 6/1988 | Okada | 340/573 |
| 4,768,023 A | 8/1988 | Xie | 340/573 |
| 4,796,014 A | 1/1989 | Chia | 340/573 |
| 4,800,370 A | 1/1989 | Vetecnik | 340/573 |
| 4,977,906 A | 12/1990 | Di Scipio | 128/885 |
| 5,036,859 A | 8/1991 | Brown | 128/734 |
| 5,074,317 A | 12/1991 | Bondell | 128/886 |
| 5,137,033 A | 8/1992 | Norton | 128/886 |
| 5,197,958 A | 3/1993 | Howell | 361/604 |
| 5,264,830 A | 11/1993 | Kline | 340/604 |
| 5,266,928 A | 11/1993 | Johnson | 340/604 |
| 5,361,627 A | 11/1994 | Levesque | 73/73 |
| 5,389,093 A | 2/1995 | Howell | 361/604 |
| 5,392,032 A | 2/1995 | Kline | 340/604 |
| 5,469,145 A | 11/1995 | Johnson | 340/604 |
| 5,469,146 A | 11/1995 | Gurler | 340/605 |
| 5,557,263 A * | 9/1996 | Fisher et al. | 340/605 |
| 5,568,128 A | 10/1996 | Nair | 340/604 |
| 5,570,082 A * | 10/1996 | Mahgerefteh et al. | 340/604 |
| 5,709,222 A | 1/1998 | Davallou | 340/604 |
| 5,760,694 A | 6/1998 | Nissim | 340/604 |
| 5,790,035 A | 8/1998 | Ho | 340/604 |
| 5,790,036 A | 8/1998 | Fisher | 340/605 |
| 5,808,554 A | 9/1998 | Shuminov | 340/604 |
| 5,838,240 A | 11/1998 | Johnson | 340/604 |
| 5,903,222 A | 5/1999 | Kawarizadeh | 340/604 |

FOREIGN PATENT DOCUMENTS

| | | |
|---|---|---|
| JP | 60213857 | 10/1985 |
| JP | 63309239 | 12/1988 |
| JP | 63311952 | 12/1988 |
| JP | 1025049 | 1/1989 |
| JP | 1277558 | 11/1989 |
| JP | 3264060 | 11/1991 |
| JP | 4012750 | 1/1992 |
| JP | 4067863 | 3/1992 |
| JP | 5137704 | 6/1993 |
| JP | 5245169 | 9/1993 |
| JP | 6300722 | 10/1994 |
| JP | 6300723 | 10/1994 |
| JP | 6300724 | 10/1994 |
| JP | 8066432 | 3/1996 |
| JP | 9033468 | 2/1997 |
| JP | 9206292 | 8/1997 |
| JP | 9294762 | 11/1997 |
| JP | 10151154 | 6/1998 |
| JP | 10272153 | 10/1998 |

OTHER PUBLICATIONS

Article titled "A Warning Detector for Urinary Incontinence for Home Health Care" in Biomedical Instrumentation & Technology 1995;29:343-349 Authors: Toshiyo Tamura PhD; Kazuki Nakajima; Takayuki Matsushita; Toshiro Fujimoto, MD; Susumu Shimooki; and Toshihiko Nakano.

Author: Inovonics Corporation Title: Technical Information Bulletin, FA203S Necklace Pendant Transmitter-Single Button. Date: 2000.

* cited by examiner

| TIME | MEASUREMENT 1 | MEASUREMENT 2 | MEASUREMENT 3 | MEASUREMENT 4 | TAG |
|---|---|---|---|---|---|
| 10:55:47 AM | 4260000 | 4260000 | 4260000 | 4260000 | 51300 |
| 11:19:01 AM | 632000 | 680000 | 634000 | 743000 | 51300 |
| 11:44:46 AM | 1140000 | 1120000 | 116000 | 1050000 | 51300 |
| 12:10:04 PM | 1670000 | 1370000 | 1640000 | 158000 | 51300 |
| 12:35:35 PM | 77600 | 76100 | 77900 | 75000 | 51300 |
| 12:59:30 PM | 28600 | 27900 | 27800 | 28800 | 51300 |
| 1:25:30 PM | 21250 | 21230 | 21260 | 21200 | 51300 |
| 1:48:49 PM | 21210 | 386 | 402 | 387 | 51300 |
| 1:50:19 PM | 416 | 387 | 419 | 387 | 51300 |
| 1:52:44 PM | 389 | 452 | 388 | 452 | 51300 |
| 1:55:13 PM | 482 | 452 | 484 | 451 | 51300 |
| 1:57:41 PM | 503 | 452 | 499 | 451 | 51300 |
| 2:00:08 PM | 484 | 452 | 483 | 516 | 51300 |
| 2:02:34 PM | 501 | 516 | 500 | 516 | 51300 |
| 2:05:00 PM | 518 | 580 | 516 | 515 | 51300 |
| 2:07:27 PM | 550 | 515 | 547 | 515 | 51300 |
| 2:10:06 PM | 532 | 515 | 531 | 515 | 51300 |
| 2:12:22 PM | 558 | 515 | 547 | 515 | 51300 |
| 2:15:02 | 555 | 515 | 547 | 579 | 51300 |
| 2:17:31 | 572 | 515 | 563 | 579 | 51300 |
| 2:20:05 | 4260000 | 4260000 | 4260000 | 4260000 | 51300 |
| 2:22:34 PM | 4260000 | 4260000 | 4260000 | 4260000 | 51300 |
| 2:25:19 PM | 4260000 | 4260000 | 4260000 | 4260000 | 51300 |
| 2:50:19 PM | 632000 | 680000 | 634000 | 743000 | 51300 |

FIG. 14

| NAME | DATE | BEGIN | END | DURATION | GROUP |
|---|---|---|---|---|---|
| Mrs. Smith | 10/12/2000 | 10:51 AM | 11:01 AM | 10 MINUTES | GROUP A |
| Mrs. Johnson | 10/12/2000 | 9:02 AM | 9:20 AM | 18 MINUTES | GROUP A |
| Mrs. Heinze | 10/13/2000 | 4:25 PM | 4:45 PM | 20 MINUTES | GROUP A |
| Mr. Hill | 10/13/2000 | 3:25 PM | 3:55 PM | 30 MINUTES | GROUP A |
| Mrs. Berg | 10/13/2000 | 8:10 AM | 8:31 AM | 21 MINUTES | GROUP A |
| Mr. Smith | 10/13/2000 | 11:07 AM | 11:30 AM | 23 MINUTES | GROUP A |

FIG. 15

WETNESS MONITORING SYSTEM

TECHNICAL FIELD OF THE INVENTION

This invention relates to a wetness monitoring system with a data collection device that attaches to a garment of an individual to gather and transmit wetness measurement data to a central computer system that determines when a wetness event occurs, notifies appropriate healthcare workers, and tracks approximate response times to ensure that the individual is consistently receiving proper care.

BACKGROUND OF THE INVENTION

Families, assisted living homes and hospitals continually strive to provide the best care they can for their loved ones, residents and patients. Yet, providing basic care such as feeding, bathing and clothing a person can be time consuming, unpleasant and unrewarding. Perhaps the least favored of these tasks is changing a diaper or garment of a person that has been rendered incontinent. Still, these tasks must be done well and in a timely manner for the person to receive proper care. Products and systems that help deliver a consistently high level of basic care can be valuable aids to the people rendering these services. Safe, economical and easy to use products and systems that help achieve these results are typically well received by families, assisted living homes and hospitals alike.

Recent nursing home industry reports indicate that about half of all nursing home residents suffer from incontinence. The healthcare workers must physically check the diapers of the residents for wetness or odor to determine if they have had an incontinent episode. Although residents are supposed to be checked every two hours, the increasing ratio of individual residents to workers makes this task increasingly difficult. Many residents end up sitting in wet or soiled diapers or garments for prolonged periods. Even when the healthcare worker performs a check every two hours, the possibility exists that the resident may remain in undesirable condition for this length of time. This is not only uncomfortable, but can cause skin irritation and breakdown, and lead to infection and more serious health problems.

Maintaining a person in a dry, comfortable condition can be difficult to achieve on a consistent basis. The person may wet or soil themselves at various times throughout the day or night. The more frequently the person is checked, the better the care they will receive. Yet, checking for wetness or excrement is an awkward and unpleasant task for everyone involved, and in a nursing home or hospital setting can be a relatively time consuming task. Less dedicated workers may avoid or skip this task. In addition, different healthcare workers may allow different degrees of wetness before they believe a change is required. These types of problems need to be quickly identified and addressed by the supervisors and managers of the institution.

A wide variety of wetness sensors and wetness monitoring systems have been developed to assist healthcare workers in detecting when a resident or patient is wet. Wetness sensors typically operate on chemical or electrical principals. Chemical sensors detect changes in chemical properties such as the pH or thermochromatic level of a bandage, diaper or garment. An example of such a chemical sensor is disclosed in U.S. Pat. Nos. 4,583,546 to Garde and 5,197,958 and 5,389,093 to Howell. The sensor turns color when contacted by urine or excrement. When a healthcare worker sees the change in color, they know the person needs attention. A problem with chemical sensors is that they are difficult to incorporate into a system that produces an audible alarm or sends a signal to a central computer where the staff and floor supervisor are located. The administrators or other staff must duplicate the work efforts of others to watch for skin rashes and sores or identify a particular worker that is skipping some checks or simply avoiding the task altogether.

Electrical sensors and monitors have been developed to detect changes in the conductive, resistive, impedance or electromagnetic characteristics of a diaper or garment due to the presence of urine. The monitors include an electric circuit that incorporates a sensor. The monitor uses the changing electrical characteristics of the sensor responsive to a dielectric fluid such as urine to determine that the diaper or garment is wet. The monitor determines that the garment is wet when the electrical circuit exceeds a threshold level inherent to its circuit. The monitor then produces a visual or audible alarm, or sends a signal to the central computer to inform the staff that the particular person wearing the monitor is wet and in need of attention. Examples of such sensors and monitors are discussed in U.S. Pat. Nos. 3,460,123 to Bass; 4,106,001 to Mahoney; 4,356,818 to Macias; 4,796,014 to Chia; 4,977,906 to DiScipio; 5,036,859 to Brown; 5,264,830 and 5,392,032 to Kline; 5,557,263 and 5,790,036 to Fisher; 5,568,128 to Nair; 5,838,240, 5,469,145 and 5,266,928 to Johnson; 5,760,694 to Nissim and 5,903,222 to Kawarizadeh, the disclosures of which are incorporated herein.

A significant problem with conventional wetness sensors and monitoring systems is that they do not gather actual wetness data. The monitors simply determine when the sensor and circuit have exceeded a predetermined threshold limit. The monitor then sounds an alarm or sends a signal to a central computer informing the healthcare staff that the particular individual needs to be changed. Actual wetness measurement data containing large quantities of information pertaining to the person condition that could prove useful to the administration and staff to provide better care to the individuals is simply not collected or lost.

Another problem with conventional wetness monitoring systems is that their sensitivity cannot be adjusted by the administration or staff to meet the needs of a particular person. The system simply detects when the electric circuit in the monitor reaches a threshold level of wetness. If a particular person has an incontinence problem involving small releases of urine or is prone to sweat during the course of their activity throughout the day, that person's monitor may continually go off even though the person does not need immediate attention. This type of nuisance alarm may cause a healthcare worker to disregard the alarm when the person actually needs attention.

A further problem with conventional wetness sensors and monitoring systems is that they require a significant amount of power to operate properly. To minimize power consumption, the monitor is designed to send signals as infrequently as possible. In many designs, the monitor will only send a signal to a central computer when a wetness event is detected. These types of systems have a significant drawback. The staff and supervisor do not know if a particular person is dry or if their monitor is simply malfunctioning.

A still further problem with conventional wetness sensors and monitoring systems is that the monitor provides no indication that the sensor is properly connected. Improperly trained or forgetful healthcare workers may incorrectly connect the sensor to the monitor. A worker may also be distracted or in a rush to perform other pending tasks and fail to connect the sensor and monitor correctly. Lack of training, distractions and the rush of performing a multitude of tasks can also prevent a worker from noticing that the monitor or sensor is damaged and not working properly. The resident or patient may end up wearing a soiled diaper or garment for many hours before the staff becomes aware of and corrects the problem.

A still further problem with conventional wetness sensors and monitoring systems is their excessive operating costs. Most conventional designs require the sensor to be disposed of after each use. Conductive and resistive type sensors that come in contact with the urine are typically disposed of after each use. These disposable sensors significantly increase the operating cost of the system because the sensors usually need to be replaced several times a day. A single person may require over a few thousand sensors annually. Even a relatively inexpensive sensor can result in high operating costs.

A still further problem with conventional wetness monitoring systems is that they are not designed to ensure that the individuals consistently receive proper care. The systems simply track the exact time between wetness events and garment changes. These systems inappropriately focus on the exact duration the individual is wet. Yet, many administrators of assisted living homes and nursing homes understand that the problem is not determining whether any given wetness event is responded to in ten or fifteen minutes, but ensuring that each individual is consistently attended to in a prompt manner and not forgotten for one or two hours or an entire day.

A still further problem with conventional wetness sensors and monitoring systems is that they are difficult to put on and uncomfortable to wear. The devices are often bulky, located in inconvenient locations on the individual that make sitting, sleeping or daily activity troublesome. Many devices include mechanisms that are elaborate and difficult to use to secure the sensor and monitor or attaching them to the garment of the individual.

The present invention is intended to solve these and other problems.

SUMMARY OF THE INVENTION

The present invention relates to a wetness monitoring system that includes a data collection device that sends wetness measurement data to a central computer that detects changes in wetness measurement data caused by the presence of urine or other dielectric fluids. The data collection device includes a semi-reusable sensor and reusable data collector that are worn on a garment of the person. The data collector includes an internal power source so that the person can live a normal ambulatory life. The data collector has an electrical circuit that uses the changing resistance characteristics in the sensor to gather wetness measurement data. The data collector periodically generates and transmits a signal containing the actual wetness measurement data. The signals are coded to identify the particular data collector or person sending the signal. The data collector is programmed to conserve power by sending signals less frequently during periods when the sensor is clearly dry. Signals are sent more frequently when the sensor is damp or a wetness event may have occurred. The central computer receives the signals containing the wetness measurement data and compares the measurement data to an adjustable wetness sensitivity level to determine if a wetness event has occurred. When the central computer determines that a wetness event has occurred, the computer displays the name of the particular person wearing the data collector and the approximate time that the wetness event occurred. The system then pages an appropriate healthcare worker to inform them that the particular individual needs attention and tracks the approximate response times to ensure that the patient is continuously receiving prompt care.

One advantage of the present wetness monitoring system is that it gathers and monitors actual wetness measurement data. The central computer monitors the actual measurement data to determine when several consecutive measurements exceed a sensitivity limit that is preselected for that particular individual to identify when a wetness event occurs. The central computer then pages the appropriate healthcare workers to inform them that the particular individual needs attention. The actual wetness data is saved and used to track approximate wetness durations and ensure that the individual is consistently receiving proper care.

Another advantage of the present wetness monitoring system is that a supervisor can easily adjust the sensitivity level of each person being monitored to ensure that the system meets the needs of each individual being monitored by the system. The supervisor can quickly and easily select one of a variety of sensitivity levels for each individual. If a particular person has an incontinence problem involving small releases of urine or is prone to sweat at particular times during their course of activity throughout the day, the sensitivity level in the central computer can be adjusted for that individual so that it will reliably determine that a wetness event has occurred when the person actually needs attention. Nuisance alarms are minimized so that the healthcare workers do not disregard or avoid responding to a page.

A further advantage of the present wetness monitoring system is that the data collector includes a power conservation circuit that minimizes the power consumption during periods when the sensor is relatively dry. The data collector is designed to send signals at periodic intervals. Signals are sent relatively infrequently when the sensor is clearly dry, and are more frequently when the sensor is damp or a wetness event may have occurred. The data collector sends signals periodically throughout the day to a central computer whether or not a wetness event is detected by the central computer. The staff and floor supervisors are informed that each data collection device is operating properly even if the individual remains dry for a relatively long period of time.

A still further advantage of the present wetness monitoring system is that the data collector indicates when it is properly connected to the sensor. A visible indicator light in the data collector flashes when the sensor is correctly secured to its data collector so that the wetness measurement circuit is working properly. The connection indicator light flashes several times to ensure that the worker sees the light even if they are momentarily distracted or in a rush to perform other pending tasks. This indication light helps minimize adverse connection of the sensor to the data collector that can arise due to lack of training, distractions and the rush the workers may experience when they are performing a multitude of tasks. This feature also helps the workers identify defective sensors or data collectors that become damaged during use.

A still further advantage of the present wetness monitoring system is that operating costs are reduced. The sensor is designed to be washed up to four times and used five times before disposal. The backing layer of the sensor is made of a durable, shrink and tear resistant material. The two spaced, conductive sensor strips are uniformly glued or otherwise secured throughout the entire top surface of the backing layer. Similarly, the absorbent layer is uniformly secured throughout the entire top surfaces of the backing layer and sensor strips. The selected materials and sensor design forms an integral sensor that maintains its shape and integrity for a limited number of uses and wash cycles. This reusability dramatically reduces the annual operating cost of the system. A person may only require a few hundred sensors on an annual basis instead of a few thousand.

A still further advantage of the present wetness monitoring system is that the sensor is easily positioned over and secured to the housing of the data collector. Two posts extend from the housing to receive one set of two corresponding holes in the sensor. The posts and holes position the sensor so that each conductive sensor strip is aligned with a contact of the data collector. A U-shaped clamp is then placed over the sensor and around the sides of the housing to hold the sensor in place. The clamp compresses the sensor against the contacts, so that the contacts pierce the backing or absorption layer and electrically engage their respective conductive strips in the sensor. This simple securement mechanism is easy to use and helps prevent operating errors when performing this rather repetitive task.

A still further advantage of the present wetness monitoring system invention is that each time the sensor is clipped to the housing of the data collector, the sensor is marked to indicate how many times that sensor has been used. The sensor is typically provided with five sets of holes. Each time the sensor is clipped to the housing, the contacts pierce or otherwise mark the sensor. These marks or indicia are located next to the set of holes that were just used to position the sensor on the housing. When the sensor is removed, these marks are easily visible to the healthcare workers. The pierce marks remain visible after the sensor is washed several times. Each time the sensor is connected to the housing of the data collector, an unmarked set of holes is inserted into the posts of the housing. The healthcare workers can use the marks and holes to easily track or otherwise determine how many times the sensor has been used. The sensor is disposed of when each of the five sets of holes has a corresponding mark.

A still further advantage of the present wetness monitoring system is that it provides a data collector designed to be reused thousands of times with minimal or no servicing. The housing hermetically seals the electronic components inside its compartment so that they are not exposed to humidity or moisture. The compartment cannot be opened without breaking the housing, which ensures that the components remain in a sterile moister free environment throughout the life of the data collector. The electrical contacts that extend from the housing are also protected by a sensor fastening member or clamp. The housing and clamp are designed to ensure that the contacts are not bent when the clamp secures the sensor to the housing and in electrical engagement with the contacts. The housing includes a pair of alignment posts that ensure the contacts are properly aligned with the sensor strip and clamp when the clamp is secured. The clamp and posts also lock the sensor strip in place so that the contacts are not bent should a person inadvertently attempt to pull the sensor strip out of engagement with the data collector without first releasing the clamp.

A still further advantage of the present wetness monitoring system is that it focuses on ensuring that every individual being monitored consistently receives proper care. The system does not focus on tracking the exact time between a wetness event and a garment change. Instead, the system is designed to meet the overall management needs of assisted living home and nursing home administrators to assure that each individual is consistently attended to in a prompt manner and not continuously forgotten for several hours or an entire day.

A still further advantage of the present wetness monitoring system is that the sensor and data collector components are relatively easy to put on and comfortable to wear. The sensor is soft to the touch and very flexible to conform to the contours of the body of the individual. The data collector is relatively small and light weight, and designed to be located near the abdomen of the individual so that it is not readily noticed when walking, running, sitting or reclining.

Other aspects and advantages of the invention will become apparent upon making reference to the specification, claims and drawings.

BRIEF DESCRIPTION OF THE DRAWINGS

FIG. 1b is an overhead view of the assisted living home of FIG. 1a.

FIG. 10b is a top, cross-sectional view of the data collector of FIG. 10a.

FIG. 12b is a flow chart showing the remainder of the programming of FIG. 12a.

Figure 1A:
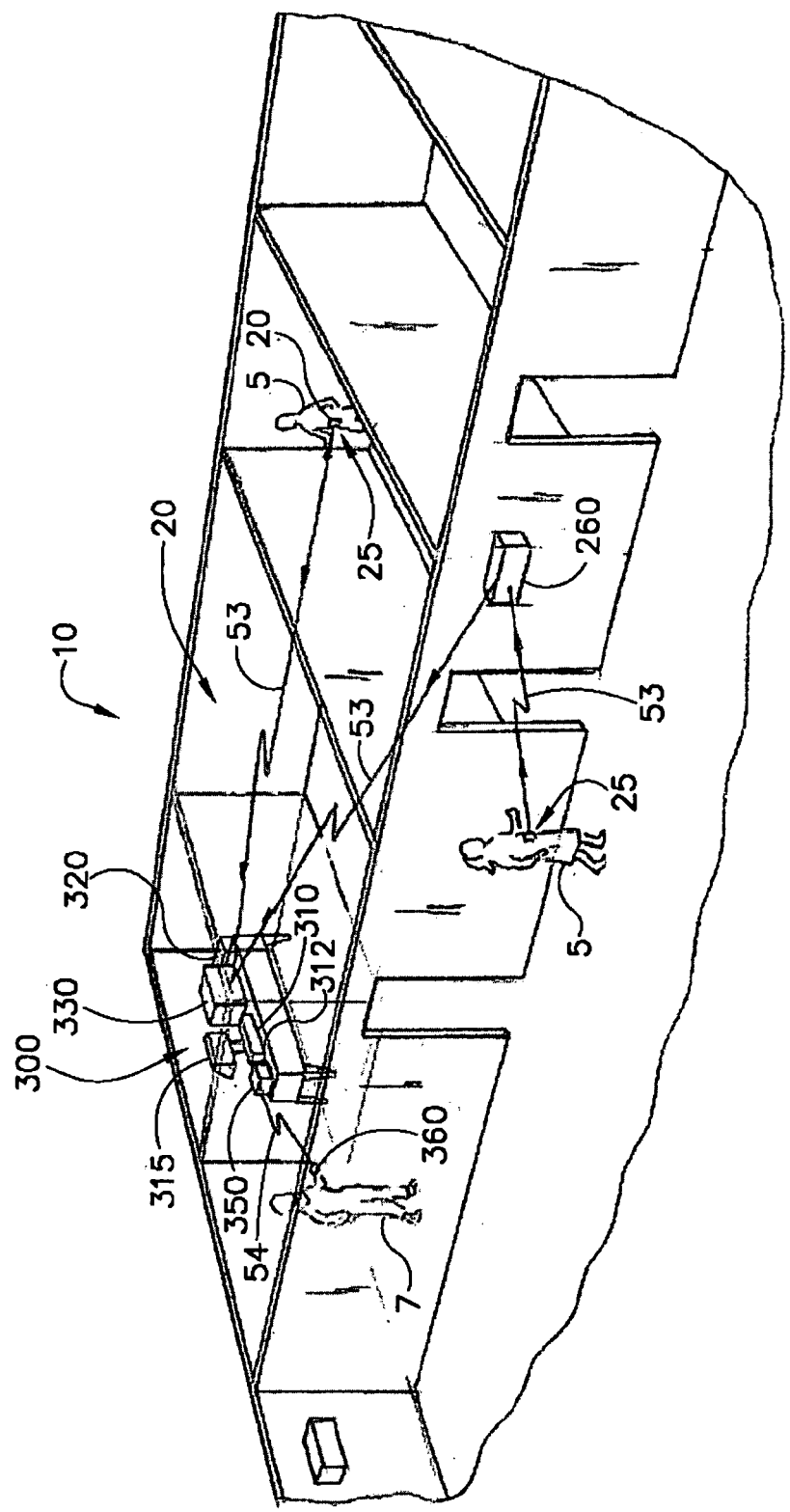
FIG. 1a is a perspective view of an assisted living home installed with the present wetness monitoring and detection system invention were the residents are wearing data collection devices that collect wetness measurement data and send coded signals containing that measurement data to a central computer that determines when a wetness event has occurred, displays this event on a computer monitor and pages an appropriate healthcare worker.

FIG. 14 is a table showing the wetness or resistance measurement data gathered by the data collector for a particular person and stored in the memory of the central computer system.

FIG. 15 is a table showing a report generated by the central computer system identifying several particular individuals using the system and the approximate times of their wetness and garment change events.

DESCRIPTION OF THE PREFERRED EMBODIMENTS

While this invention could take on a variety of different embodiments and forms, the drawings show and the specification describes a preferred embodiment. However, it should be understood that the drawings and specification are to be considered an exemplification of the principles of the invention, and are not intended to limit the broad aspects of the invention to the embodiment illustrated and discussed.

Many individuals 5 desire or need assistance from healthcare workers 7 such as nurses, nurses aids, nutritionists, cooks, doctors, etc. These individuals live in assisted living or nursing homes 10, and are frequently afflicted with bladder control problems that hinder their ability to notice when their bladder is full or exert the control needed to hold their bladder until they are able to use a bathroom. The consequence of this affliction is that the individual 5 ends up wetting his or her undergarment or diaper 15 worn around the waist and groin of the individual. Above and beyond the embarrassing and awkward situation this affliction creates, this affliction presents a personal hygiene problem that can lead to the irritation and breakdown of the skin when left unattended for a significant amount of time.

Figure 2:
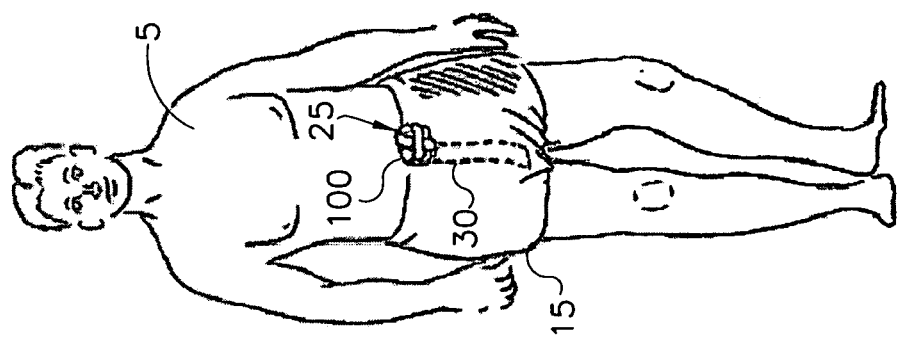
FIG. 2 is a view of an individual wearing a garment and the wetness measurement data collection device formed by a sensor and a data collector.
Figure 1B:
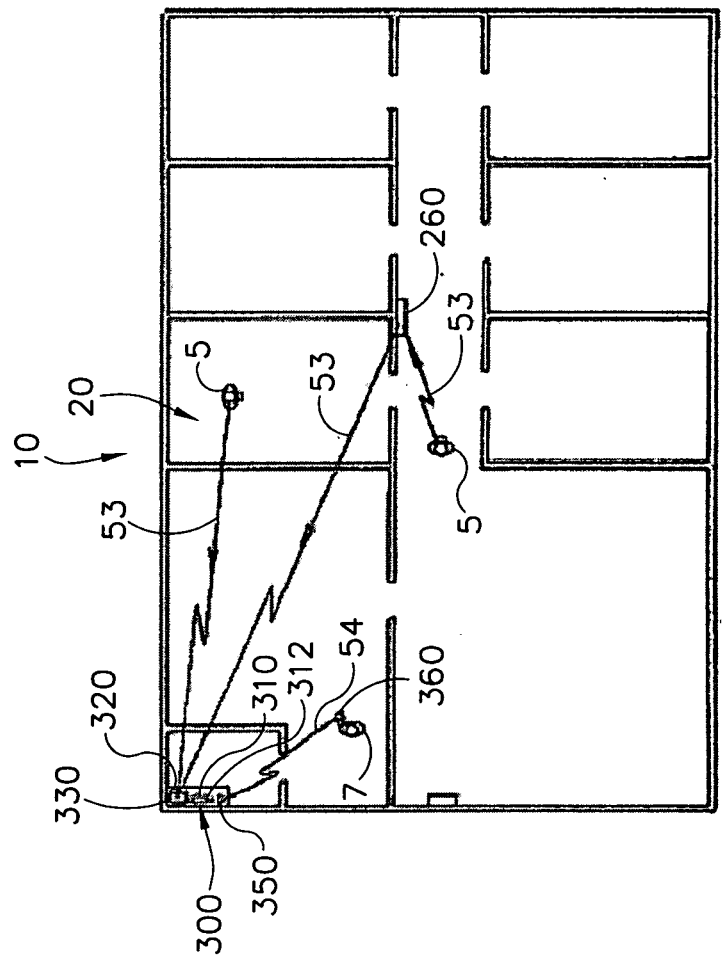

The present invention pertains to a wetness monitoring system that is generally referred to by reference number 20. As shown in FIGS. 1a, 1b and 2, the wetness monitoring system 20 includes a wetness measurement collection device 25 formed by a semi-reusable sensor 30 and a reusable data collector 100. The data collector 100 is equipped with a transmitter that periodically sends the measurement data to a central computer system 300 to determine when a wetness event occurs. As discussed below, the data collection device 25 is secured to or worn on the garment 15 of the individual. Although the wetness sensing system 20 is shown and described as being used for a number of individuals 5, it should be understood that the system could be adapted for one or two individuals in a single family home environment without departing from the broad aspects of the invention.

Figure 4:
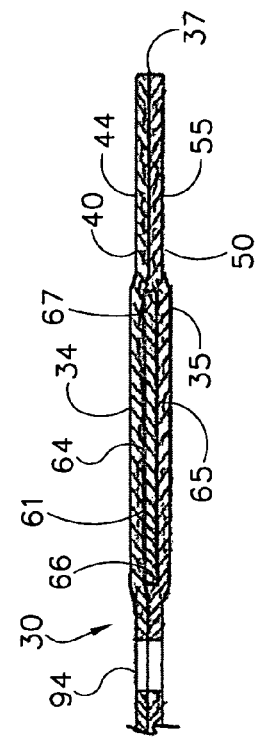
FIG. 4 is a cross-sectional view of FIG. 3 taken along lines 4-4 showing one of the conductive strips sandwiched and enclosed between the absorbent pad and backing layer.
Figure 3:
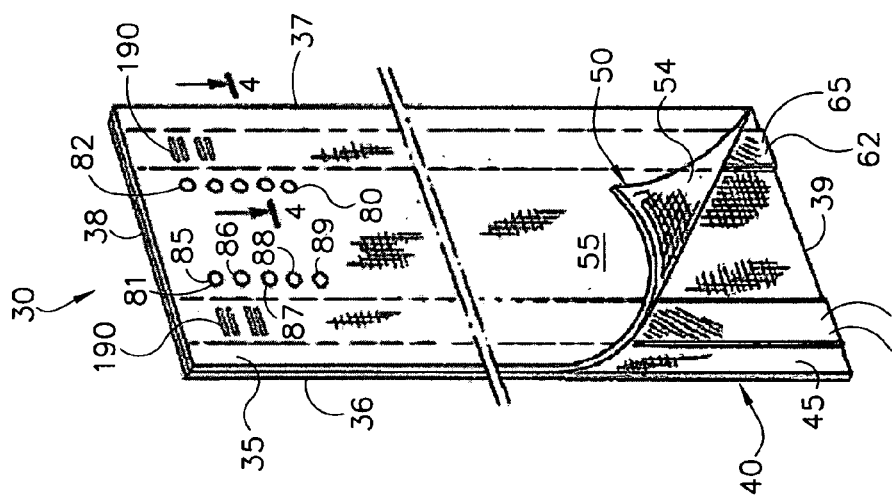
FIG. 3 is a perspective view of the sensor strip having an absorbent layer, two spaced conductive strips, and a backing layer, and one end of the sensor strip having five sets of holes, two sets of holes being marked to indicate that the sensor has been used twice.

As shown in FIGS. 3 and 4, the sensor or sensing strip 30 has upper and lower surfaces 34 and 35, substantially parallel side edges 36 and 37 and ends 38 and 39. The sensing strip 30 includes an absorbent pad 40, a backing sheet 50 and two spaced, substantially parallel, conductive strips 61 and 62. The absorbent pad 40 is designed to absorb a liquid or an amount of wetness. The conductive strips 61 and 62 are spaced apart a relatively constant or uniform distance of about 1.5 inches down the length of the sensor 30 to produce an amount of resistance between the conductive strips. The sensor 30 produces an actual wetness value indicative of the amount of wetness absorbed by the absorbent material 40 between the conductive strips 61 and 62 at a given point in time, as discussed below.

The absorbent pad 40 is formed by a sheet of soft, flexible, highly absorbent material that does not irritate or sensitize human skin, and is preferably a polyester product manufactured by Avery as product 5322P. The absorbent pad 40 is highly porous, breathable, and freely passes air and moisture. The pad 40 includes top and bottom surfaces 44 and 45. The backing sheet 50 is a paper thin, highly flexible, shrink resistant, and tear resistant material, and is preferably a polyethylene product manufactured by DuPont as Tyvek® 1443R. The backing sheet includes top and bottom surfaces 54 and 55. The absorbent pad 40 and backing sheet 50 are substantially nonconductive when free from sweat, tap water, urine and other conductive materials.

Each conductive sensor strips 61 and 62 is formed by a strip of flexible, corrosive resistant, conductive material, such as a woven nylon or polyester fabric coated with copper or nickel manufactured by Monsanto as Flectron™. Each strip 61 and 62 has top and bottom surfaces 64 and 65 and inner and outer edges 66 and 67. Each strip 61 and 62 has a width of about ¼ of an inch between edges 66 and 67. The outer edge 67 of each strip 61 and 62 is about ¼ inch from its respective edge 36 or 37 of the sensor 30.

The sensor strips 30 are manufactured in roll form by bonding the absorbent pad 40, backing layer 50 and conductive strips 61 and 62 together to form an integral strip. During manufacture, a first adhesive coating (not shown) is applied across the entire bottom surface 45 of the absorbent pad 40. The conductive strips 61 and 62 are then rolled onto or otherwise laid against the adhesive on the bottom surface 45 so that the top surface 64 of each strip engages the bottom surface of the pad 40. The adhesive firmly secures each strip 61 and 62 to the pad 40. A second adhesive coating (not shown) is applied across the entire surface 54 of the backing layer 50, except for about an ⅛ of an inch portions extending along its longitudinal edges. The first and second adhesive coatings combine to cover the entire top and bottom surfaces 64 and 65 of conductive strips 61 and 62. The adhesive is preferably an acrylic copolymer that is not irritating or sensitizing to humans.

The backing layer 50 is rolled onto or otherwise laid against the pad 40 and strips 61 and 62 so that the top surface 54 of the backing layer engages the bottom surfaces 45 and 65 of the pad 40 and strips 61 and 62. The adhesive coatings firmly secure the backing layer 50 to the pad 40 and strips 61 and 62. The conductive strips 61 and 62 are sandwiched between and enclosed or encased by the pad 40 and backing layer 50. The backing layer 50 is preferably about 1/32 of an inch wider than the pad 40 so that the adhesive layer applied to the pad is completely covered by the backing layer 50 during the manufacturing process. The pad 40, backing layer 50 and conductive strips 61 and 62 are bonded or otherwise secured together to form a roll of the integral sensor strip 30. This roll is then cut into strips 30 having a length of 24 inches. The individual sensor strips 30 have a width of about 2.5 inches, and a thickness of about 0.01 of an inch. It should be understood that the sensor strips 30 can be manufactured to different lengths and widths to accommodate different size individuals, such as adults and children.

Ten holes 80 are punched through each sensor strip 30. The holes 80 are located near the end 38 of the sensor 30 to be secured to the data collector 100, as discussed below. Each hole 80 has a diameter of about 3/16 of an inch and extends completely through the pad 40 and backing layer 50, but does not engage the conductive strips 61 and 62 which remain enclosed between the pad and backing layer. Half of the holes 81 are located in a row extending along one side 36 of the strip 30 near the inside edge 66 of conductive strip 61, and half of the holes 82 are located in a row extending along the other side 37 of the strip near the inside edge of the other conductive strip 62. The holes 80 are arranged to form five sets of holes 85-89. Each set 85-89 includes one hole 81 near conductive strip 61 and one hole 82 near conductive strip 62. Although the sensor strip 30 is shown and described as having five sets of two holes for a total of ten holes, it should be understood that the sensor could have fewer or more sets of holes without departing from the broad aspects of the invention. It should also be understood that each set of holes could be formed by more than two holes or could be a single hole without departing from the broad aspects of the invention.

Figure 5:
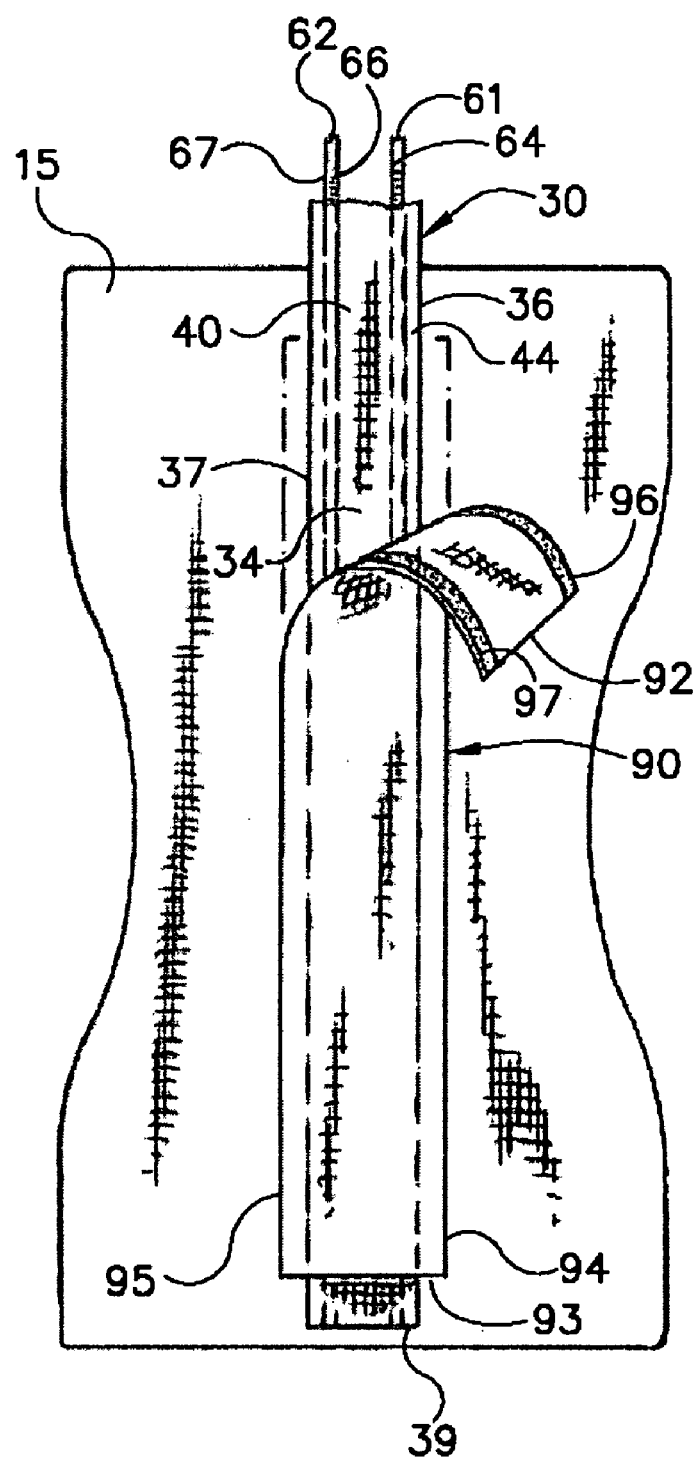
FIG. 5 is a perspective view showing the sensor strip secured to the garment via a positioning sheet.

As shown in FIG. 5, the sensor 30 is laid on the inside surface of the garment 15 with the absorbent pad 40 preferably facing toward the skin of the person 5 and the backing layer 50 facing the garment 15. However, it should be understood that the collecting device 25 will operate effectively if the backing layer 50 faces the skin of the person 5. A positioning sheet 90 can be used to maintain the sensor 30 in proper alignment on the garment 15 during use. The positioning sheet 90 also acts as a shield for the sensor strip 30 to help keep solid waste off of or adhering to the sensor strip during use. The positioning sheet 90 has two opposed ends 92 and 93 that define its length and two opposed parallel edges 94 and 95 that define its width. The width of the positioning sheet 90 is larger than the width of the sensor strip 30. The positioning sheet 90 is placed over the sensor strip 30 so that the outer edges 94 and 95 straddle or extend beyond the edges 36 and 37 of the sensor strip 30. Two adhesive coating strips 96 and 97 are applied to a bottom surface of the positioning sheet 90. Each coating strip 96 and 97 extends the length of the sheet 90 along one of its outer edges 94 and 95. These adhesive coatings 96 and 97 secure the positioning sheet 90 to the garment 15. The sensor strip 30 is maintained between the edges 94 and 95 of the positioning sheet 90 to ensure that the sensor is maintained against a location of potential wetness such as the groin area of the individual 5 during use. The positioning sheet 90 is a very thin sheet of liquid permeable material that is not irritating or sensitizing to humans.

The data collector 100 is relatively small and compact as shown in FIGS. 6-9. The outer margins of the data collector 100 are generally defined by its housing 102. The housing 102 includes a shell 104 that forms the front wall 105 and sidewalls 106-109 of the housing, and a lid 110 that forms the back wall 112 of the housing. The corners and edges of the shell 104 are rounded for comfort. The lid 110 is relatively flat. The shell 104 and lid 110 are made of a rigid, shatter-proof material such as a polycarbonate plastic. The shell 104 and lid 110 are joined together to form a water tight, interior chamber or enclosure 115 that contains and protects various electrical components inside. The housing 102 preferably has a height of about 1.25 inches from front 105 to back 112, a length of about 4 inches from side 106 to side 107, and a width of about 2 inches from side 108 to side 109. The housing 102 is preferably transparent to allow the healthcare workers 7 to see an indicator light sealed inside the chamber 115, as discussed below. The sidewalls 106-109 of the shell 104 extend below the bottom wall 112 of the lid 110 to form a lip 116 extending around the lid.

Figure 6:
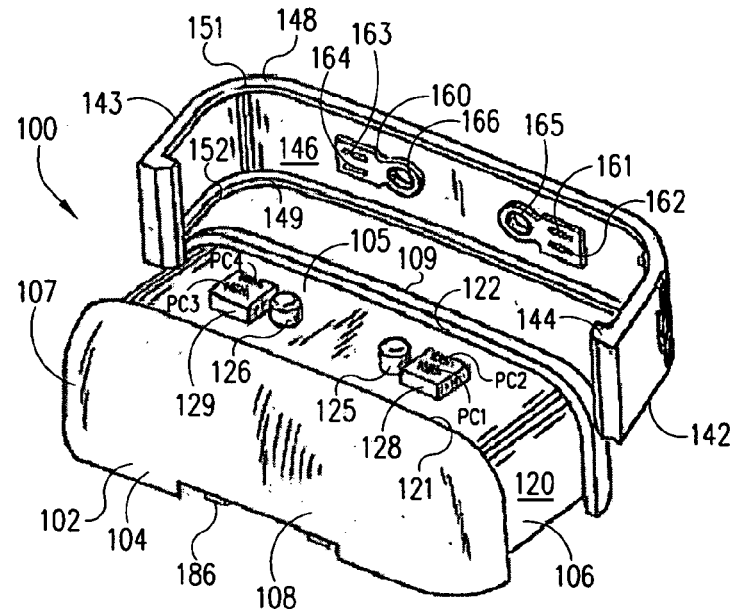
FIG. 6 is a top, perspective view of the data collector with the sensor clamp in a release position and rotated to show its recesses on its inside surface.

The outer surface of the shell 104 has a continuous channel 120 extending into the front wall 105 and sidewalls 106 and 107, as best shown in FIG. 6. The channel 120 is bounded by brims 121 and 122 and has a width of about one inch and as a depth of about ⅛ of an inch. Two posts 125 and 126 project perpendicularly from the front wall 105 and extend into the channel 120. The posts 125 and 126 are an integral part of the shell 104 and are spaced about one inch apart, each post being symmetrically spaced about a half inch from the center of the shell. Two platforms 128 and 129 also project from the front wall 105 and extend into the channel 120. The platforms 128 and 129 are an integral part of the shell 104 and are located just outside of the posts 125 and 126. The platforms 128 and 129 are spaced about 1.5 apart to coincide with the distance between conductive strips 61 and 62.

Conductive contacts PC1-PC4 are embedded in and extend completely through the front wall 105 of the housing 102. The contacts PC1-PC4 are preferably made of beryllium copper. The outer ends 135 of the contacts PC1-PC4 are barbed. Each barb has a relatively sharp point or tip. A first set of spaced contacts PC1 and PC2 project out from platform 128, and a second set of spaced contacts PC3 and PC4 project out from platform 129. The contacts PC1-PC4 extend perpendicular to the front wall 105 and parallel to the posts 125 and 126. The posts 125 and 126, platforms 128 and 129, and contacts PC1-PC4 extend out of the channel 120 slightly beyond the outer surface of the front wall 105. The posts 125 and 126 preferably extend slightly farther out than the tips of the barbed contacts PC1-PC4.

The housing includes a fastener or clamp 140 to removably secure the sensor strip 30 to the data collector 100. The clamp 140 has a U-shape with a middle portion 141 and two perpendicular legs 142 and 143. Each leg 142 and 143 has a free end with an inwardly extending flange 144. The clamp 140 has inside and outside surfaces 146 and 147, and side edges 148 and 149. The clamp 140 is sized and shaped to be relatively smoothly or flushly received by channel 120. Along the length of each side edge 148 and 149 of the clamp 140 is a rim 151 or 152. The rims 151 and 152 have a thickness of about ⅛ of an inch, or roughly the same as the depth of the channel 120. The width of the clamp 140 is about ³¹⁄₃₂ of an inch, just slightly less than the width of the channel 120. The length of the clamp is about 3.25 inches, or roughly the same as the length as the shell 104. The clamp 140 is made of a resilient plastic that allows it to be snap fit into the channel 120 of the housing 102. The length of the legs 142 and 143 is such that each flange 144 snap fits around and abuts against the lid 110 when the clamp 140 is inserted into the channel 120. This snap fit holds the clamp 140 snug inside the channel 120 and secures it to the housing 102. Although a clamp 140 is shown and described to secure the sensor to the data collector 100, it should be understood that other types of fasteners could be used without departing from the broad aspects of the invention.

The inside surface 146 of the clamp 140 has two symmetrical, slightly thicker, raised areas 160, as best shown in FIG. 6. Each raised area 160 has two sets of slit recesses 161 and 162 or 163 and 164. The slit recesses 161 and 162 receive the tips of the barbed contacts PC1 and PC2 when the clamp is secured to the housing 102. The slit recesses 163 and 164 receive the tips of the barbed contacts PC3 and PC4. Each raised area 160 also has a pair of round recesses 165 and 166 for receiving the top of the posts 125 and 126. The outer ends of the posts 125 and 126 are slightly rounded to help them align with and slide into their respective recess 165 or 166. As stated above, the posts 125 and 126 preferably extend slightly further out than the ends of the barbed contacts PC1-PC4, The posts 125 and 126 act as a guide to ensure that the barbed tips 135 of the contacts PC1-PC4 are properly aligned with and received by their recesses 161-164. The slightly longer posts 125 and 126 engage the raised area 160 of the clamp 140 before the barbed tips 135 to help ensure that the tips are not compressed against, bent or otherwise damaged by the inside surface 146 of the clamp 140 when the clamp is snap fit onto the housing 102. When the clamp 140 is secured to the housing 102, the outer ends of the posts 125 and 126 bottom out in their respective recesses 165 and 166, and prevent the barbed tips 135 of contacts PC1-PC4 from bottoming out in their recesses 161-164 to provide additional protection to the barbed tips.

Figure 9:
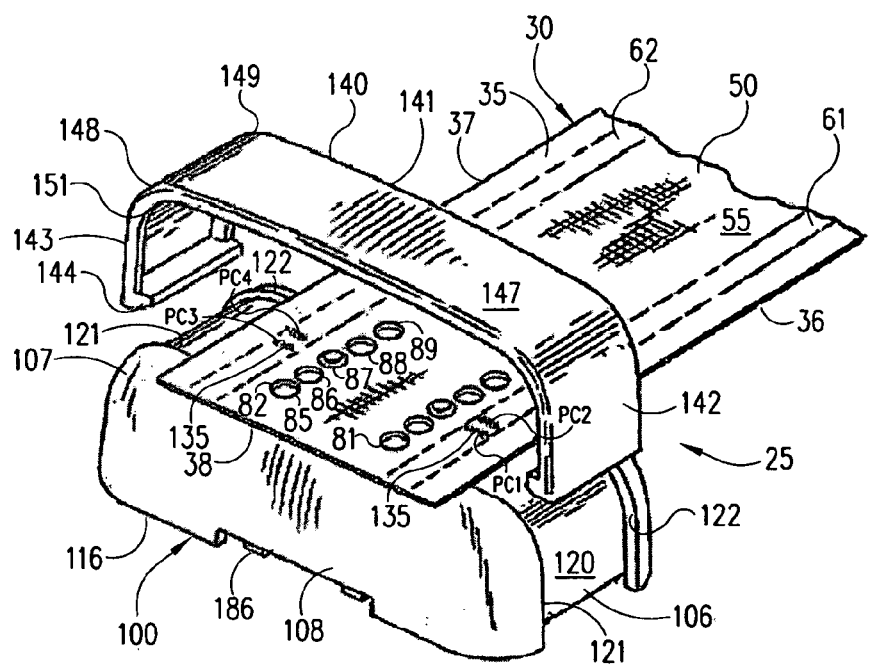
FIG. 9 is a perspective view showing the sensing strip aligned over the housing of the data collector with one set of holes receiving the posts and each conductive strip being pierced by one set of barbed contacts, and showing the sensor clip in an aligned position just prior to fastening the sensor strip to the housing.

As shown in FIG. 9, the sensor strip 30 is secured to the data collector 100 by removing the clamp 140 to a release position and placing the strip over the front 105 of the housing 102. The sensor strip 30 is then aligned with the data collector 100 by laying the sensor flat over the front wall 105 and perpendicular to channel 120, and inserting posts 125 and 126 through one set of holes 85, 86, 87, 88 or 89. This aligns each conductive strip 61 and 62 over one of the two platforms 128 and 129 and sets of barbed contacts PC1 and PC2 or PC3 and PC4. The absorbent pad 40 is preferably facing down against the front 105 of the housing 102 with the backing layer 50 facing away from the housing. If desired, the healthcare worker 7 can press against an area of the backing layer 50 directly over the barbed contacts PC1-PC4 so that each barbed contact pierces into the pad 40 to help hold the sensor strip 30 in place while aligning and securing the clamp 140 in place. Although the sensor 30 is shown and described as laying with the pad 40 facing the channel 120 and the backing layer 50 facing the clamp 140, it should be understood that proper securement and electrical engagement can be achieved when the sensor is flipped over with the backing layer facing the channel.

Figures 7, 8:
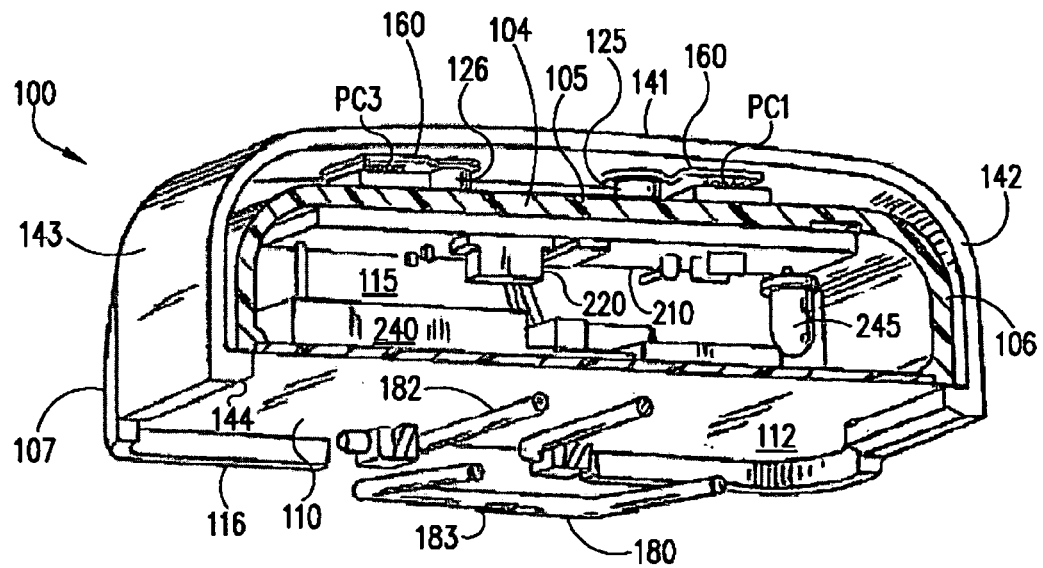
FIG. 7 is a side, cross-sectional view of the data collector with its sensor clamp in a secure position and showing its internal electrical components.
FIG. 8 is a bottom, perspective view of the data collector showing its garment clip.

Once the sensor 30 is properly aligned over the housing 102, the clamp 140 is used to lock the sensor in place. The clamp 140 is moved to its aligned position shown in FIG. 9. The side edges 148 and 149 of the clamp 140 are parallel to the channel 120 so that legs 142 and 143 enter the slots formed by the channel in sidewalls 106 and 107. The middle 141 of the clamp 140 is then pushed toward and down into the channel 120. The legs 142 and 143 slide along the portion of the channel formed in the sidewalls 106 and 107 until the flanges 144 snap fits around the lid 110 and the posts 125 and 126 bottom out in their recesses 165 and 166. This snap fit secures the clamp 140 into its secure position as shown in FIGS. 7, 8 and 10, and locks the sensor 30 in place to the housing 102.

The snap fit of the clamp 140 secures and locks the sensor 30 to the housing 102. The sensor strip 30 is intertwined around and compressed between the brims 121 and 122 of the channel 120 and the rims 151 and 152 of the clamp 140. Posts 125 and 126 also extend through one of the sets of holes 85-89 and into their respective recesses 165 and 166 in the clamp 140. The inside surface 146 of the clamp 140 presses against the backing layer 50 of the sensor 30 to maintain the barbed contacts PC1-PC4 in their pierced orientation through the pad 40 and in electrical engagement with their respective conductive strips 61 or 62. The barb contacts PC1-PC4 either pierce entirely or partially through the sensor 30. When the contacts PC1-PC4 pierce entirely through the sensor 30, the barbs pierce the backing layer 50 and enter their respective recesses 161-164. When the contacts PC1-PC4 only partially pierce the sensor 30, the contacts deform the backing layer by pushing or otherwise forcing it into the slit recess 161-164. In either event, the sensor 30, and particularly the backing layer 50, becomes visibly and substantially permanently or otherwise lastingly deformed or marked as a result of being secured to the data collector 100 by the clamp 140. The sensor 30 remains visibly marked when the clamp 140 and sensor are removed from the data collector 100 and the sensor is cleaned, as discussed below.

The wetness data collecting device 25 formed by the joined and electrically connected sensor 30 and data collector 100 is now ready to be placed on and secured to the garment 15 of the individual 5. The data collector 100 is removably secured to the garment 15 of the individual 5 by a belt clip 180. The belt clip 180 is made of a resilient strand 181 of nonconductive and non-corrosive material, such as music wire with a black zinc dichromate coating. As best shown in FIG. 8, the clip 180 has two U-shaped legs 182 and a single U-shaped middle or outer portion 183. Each leg 182 lays flat against the outer surface of the back wall 112 of the lid 110, and has first and second ends 184 and 185 that are secured to the back wall via L-shaped mounting brackets 186 and 187. The brackets 186 and 187 extend from the outer surface of the back wall 112 and are an integral part of the lid 1.10. The two brackets 186 closest the sidewall 108 have an open end facing that sidewall 108. The two opposed brackets 187 closest the sidewall 109 have an open end facing that sidewall 119. The diameter of the metal strand forming the clip 180 is slightly larger than the openings of the brackets 186 and 187 so that the ends of the legs 182 are snuggly received by the openings in the brackets. The U-shape of the legs 182, the orientation of the opposed facing brackets 186 and 187, and the relative sizes of the legs and open ends of the brackets combine to secure the clip 180 to the lid 110. The middle or outer portion 183 of the clip 180 is formed in a folded back position to extend over the legs 182. The outer portion 183 is biased so that its top 189 presses or pinches down on the legs 182, brackets 186 or back wall 112 of the lid 110. Although a clip 180 is shown and described to secure the data collector 100 to the garment 15, it should be understood that other types of fasteners could be used without departing from the broad aspects of the invention.

Figure 10A:
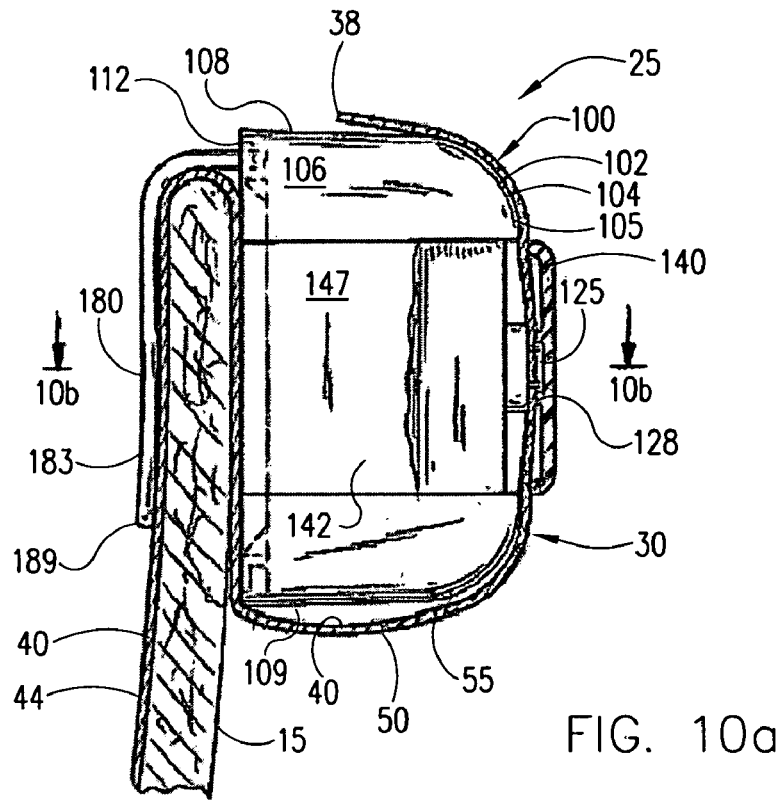
FIG. 10a is a side, partial cross-sectional view showing the data collector fastened to a garment by the garment clip, the sensor strip fastened to the data collector by the sensor clamp, and the sensor strip looped under the monitor, over the garment and down along an inside surface of the garment.
Figure 10B:
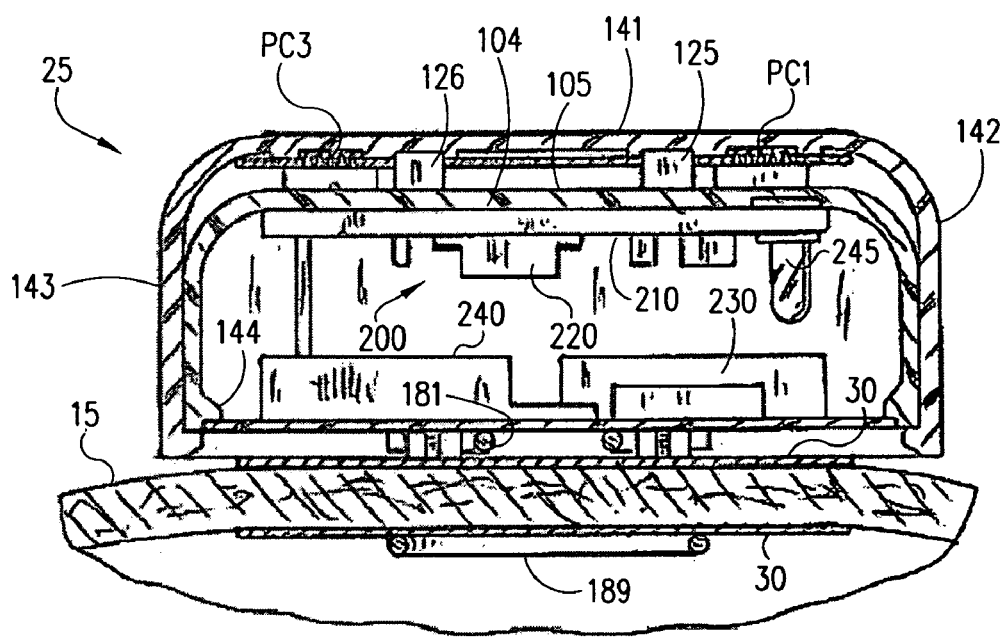

The data collector 100 is preferably secured to the garment 15 of the individual 5 by facing the back wall 112 towards the individual with the top or open end 189 of the clip 180 facing down, as shown in FIGS. 10*a* and 10*b*. The top edge of the garment 15 is then pushed or otherwise inserted between the top 189 of the outer portion 183 of the clip 180 and its legs 182. The insertion of the garment 15 causes the clip 180 to bend where the legs 182 and outer portion 183 intersect, and moves the top 189 of the outer portion away from the legs. The resilient nature of the clip 180 biases the outer portion 183 back toward the legs 182. This biasing action pinches the garment 15 between the outer portion 183 and the legs 182, brackets 186 or back wall 112 of the lid 110, and secures the data collector 100 to the garment and the individual 5. As noted above, a positioning sheet or shield 90 can be used to maintain the sensor strip 30 in a desired position on the garment 15.

The data collection device 25 is easily removed from the garment 15 of the individual 5 by simply releasing the garment from the clip 180. The sensor strip 30 is removed from between the positioning sheet or shield 90 and the garment 15 by pulling its end 38. The sensor 30 is removed from the data collector 100 by removing the clamp 140 and pulling or otherwise removing the sensor 30 out of its pierced engagement with the barbed contacts PC1-PC4. As noted above, the piercing or compressing engagement of the barbed contacts PC1-PC4 leaves a number of visible marks 190 in the sensor 30. The marks 190 are formed next to the selected set 85, 86, 87, 88 or 89 of holes 80 through which the posts 125 and 126 passed when the sensor was secured in place by the clamp 140. The marks 190 are formed by each of the two holes 81 and 82 forming the selected set of holes.

The marks or indicia 190 in the sensor 30 remain even after the sensor has been washed or otherwise sanitized and reused several times. Each time the sensor strip 30 is used, the posts 125 and 126 are aligned with a different, previously unused and thus unmarked, set of holes 85-89. The healthcare worker 7 can track or otherwise determine how many times a sensor 30 has been used by noting how many sets of holes 85-89 have a mark 190 by them. For example, FIG. 3 shows a sensor that has been used twice as indicated by the marks 190 by two sets of holes 85 and 86. The sensor 30 is designed to have a life span that will withstand four washings so that the sensor can be used five times. When marks 190 appear by each of the five sets of holes 85-89, the healthcare worker 7 is instructed to dispose of the sensor or otherwise remove it from further use.

Figure 11:
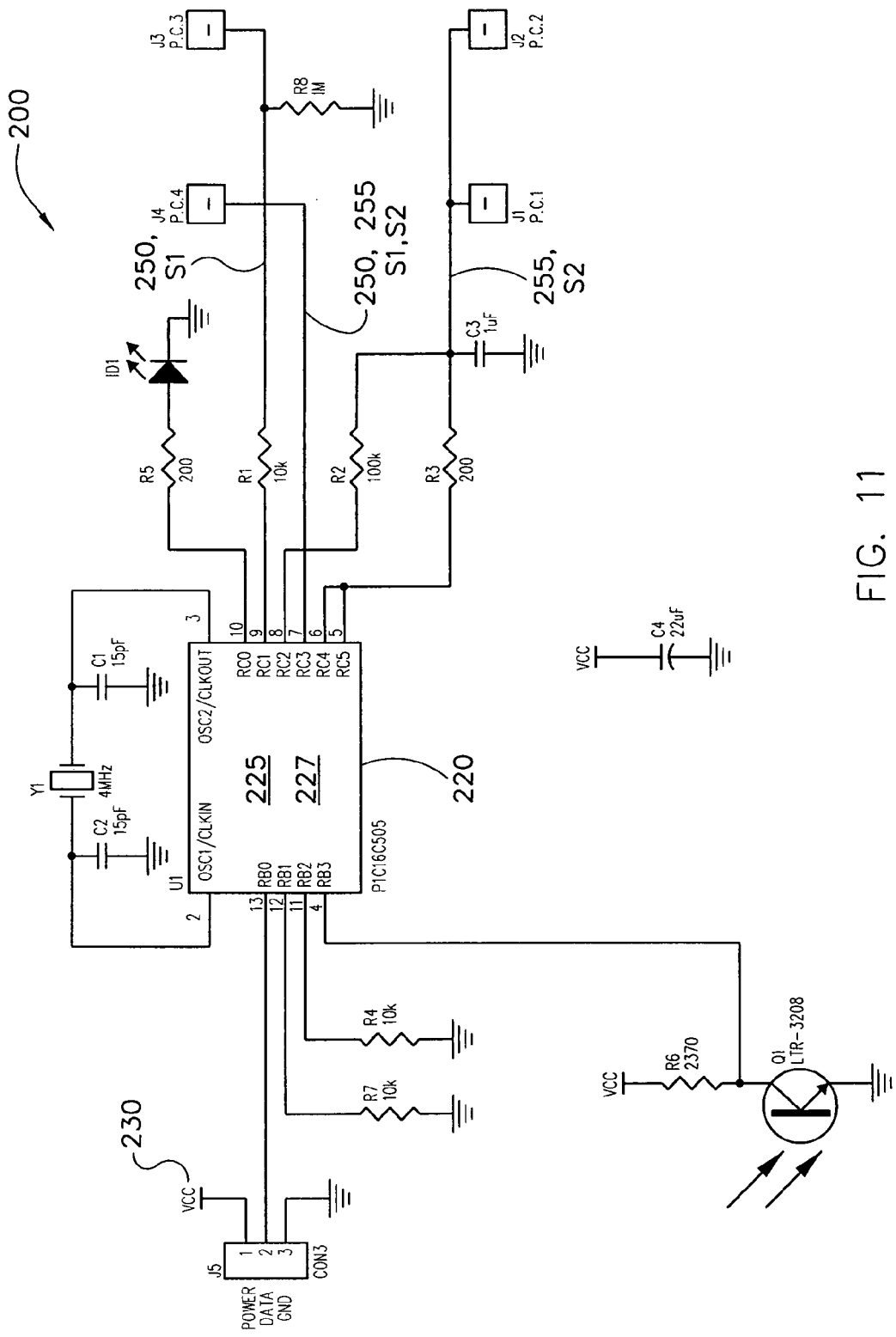
FIG. 11 is an electrical schematic of the data collector.

The data collector 100 has an electrical circuitry 200 shown in FIG. 11. The circuitry 200 includes components such as a circuit board 210, a processor 220 with an associated memory 225 and clock 227, a power source such as a battery 230, and a communication device such as a transmitter 240. As noted above, these components are sealed inside the chamber 115 of the housing 102 and firmly secured to the shell 104 as shown in FIG. 7. The circuitry 200 also includes the contacts PC1-PC4 embedded in the housing 102 and their exposed barbed tips 135. The processor or microcontroller 220 is preferably sized for mounting on the circuit board 210 with a 14-pin SOIC footprint, and is protected by a watchdog timer. The processor 220 is programmed as in FIGS. 12a and 12b. The data collector 100 has an approximate battery life of one year, assuming a 63% duty cycle or 15 hours of use per day. The data collector 100 is not intended to be serviceable, and the battery 230 is not intended to be replaceable. At end of its service life, the data collector 100 is simply thrown away or otherwise taken out of service.

The circuitry 200 includes a sensor detection circuit 250 that allows the processor 220 to determine when the sensor 30 is properly attached to the data collector 100. As shown in FIG. 11, the sensor detection circuit 250 includes ports RC1 and RC3, contacts PC3 and PC4 and resister R1. The processor 220 periodically applies a 3-volt potential or signal S1 to port RC3 every few seconds (e.g., about every 2-3 seconds). When the sensor 30 is properly attached to the data collector 100, contacts PC3 and PC4 are both in electrical communication with conductive strip 62. The 3-volt signal travels from port RC3 to contact PC4, from contact PC4 through conductive strip 62 and to contact PC3, and from contact PC3 back to the processor via resister R1 and port RC1. When the processor 220 senses the signal S1 at port RC1, the processor determines that a sensor 30 is properly attached to the data collector 100. The processor 220 is programmed to continue periodically applying the signal S1 at port RC3 and to continue looking for the signal at port RC1 to ensure that the sensor 30 remains properly attached to the data collector 100.

Figure 12A:
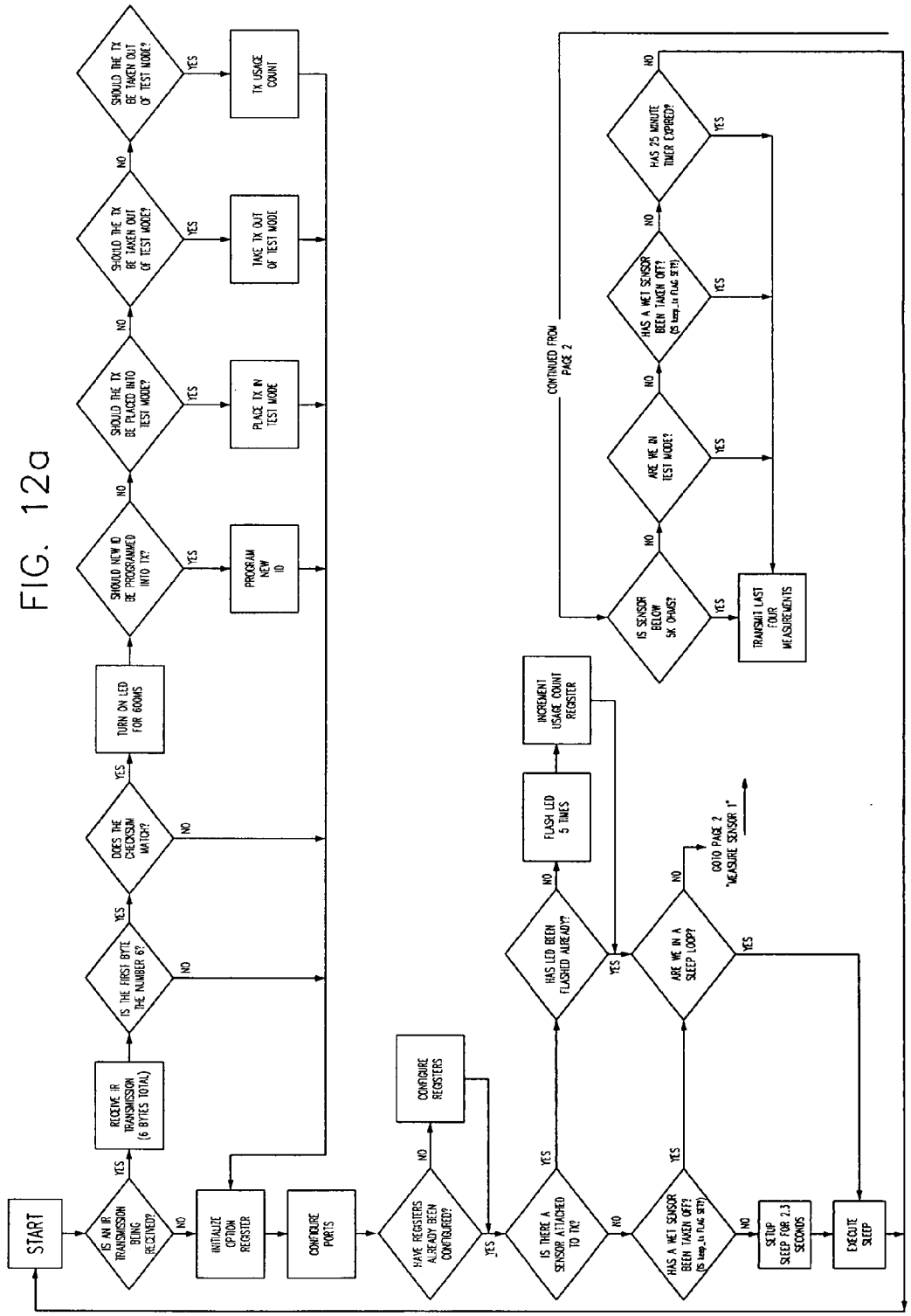
FIG. 12a is a flow chart showing much of the programming for the data collector.
Figure 12B:
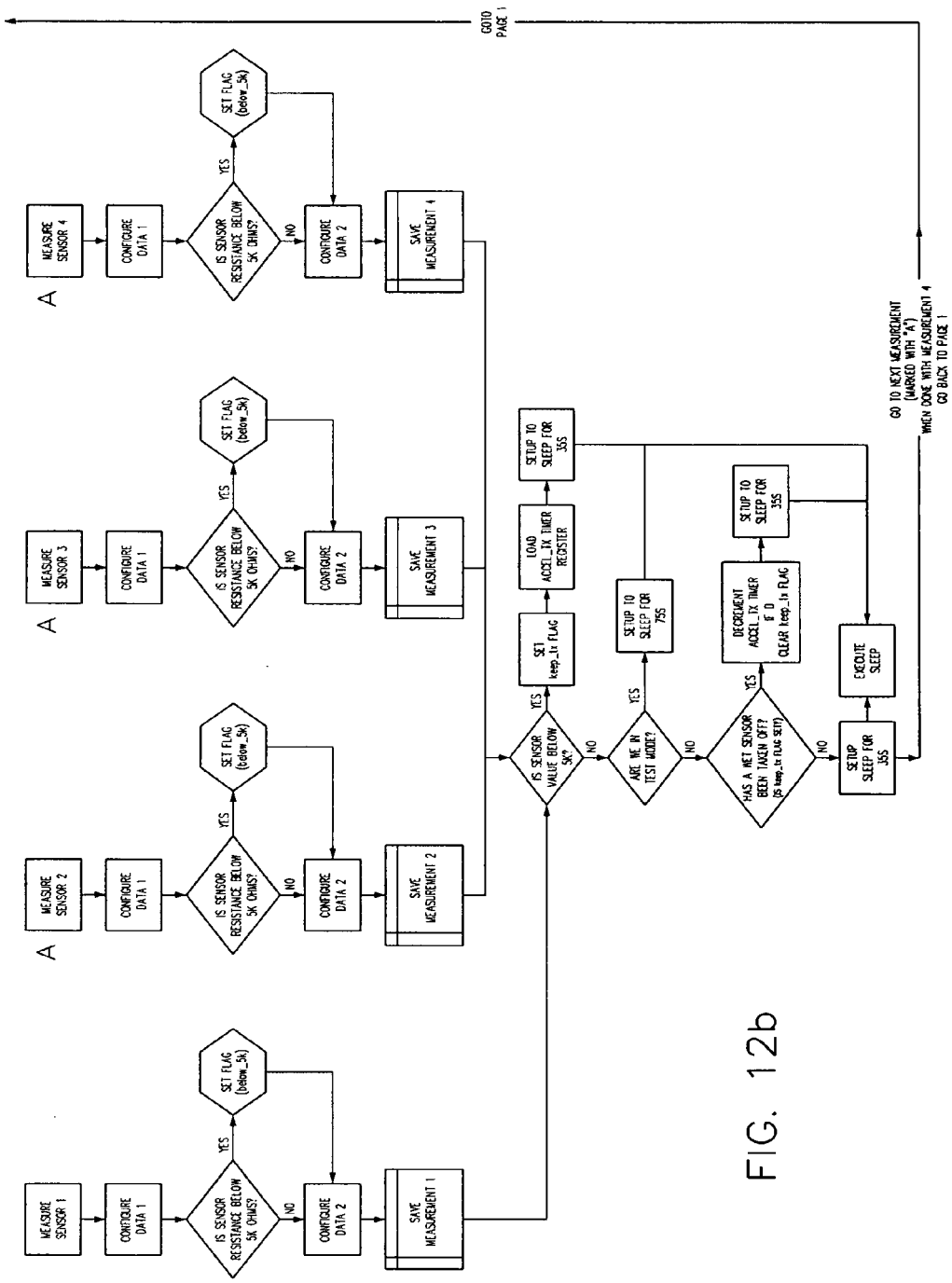

The processor 220 is programmed to use the sensor detection circuit 250 to determine when a new or clean sensor 30 is attached to the data collector 100. Before a new sensor 30 can be attached, the used, wet, damp, or otherwise soiled sensor must be removed. When the used sensor 30 is removed, no sensor is attached to the data collector 100 and the processor 220 will not receive signal S1 at port RC1 even though the signal is still being sent via port RC3. As indicated in FIGS. 12a and 12b, the processor 220 is programmed to sets a flag F1 in the absence of receiving signal S1 at port RC1. This flag F1 is used in the programming to indicate that no sensor 30 is present or attached to the data collector 100. When the flag F1 is set and a new, dry or otherwise clean sensor 30 is secured to the data collector 100 in a proper manner, the processor 220 begins receiving signals S1 at port RC1 and is programmed to determine that a new sensor 30 has just been attached to the data collector. The processor 220 then sets the flag F1 in its programming to indicate that the new sensor 30 is attached to the data collector 100, and activates an indicator light 245 inside the chamber 115 of the data collector 100 as indicated in FIG. 12a. The indicator light 245 flashes on and off about five times, for about ten seconds, to give the healthcare worker 7 time to observe the light. This flashing indicator light 245 informs the healthcare worker that the sensor 30 is properly attached to the data collector 100.

Figure 13:
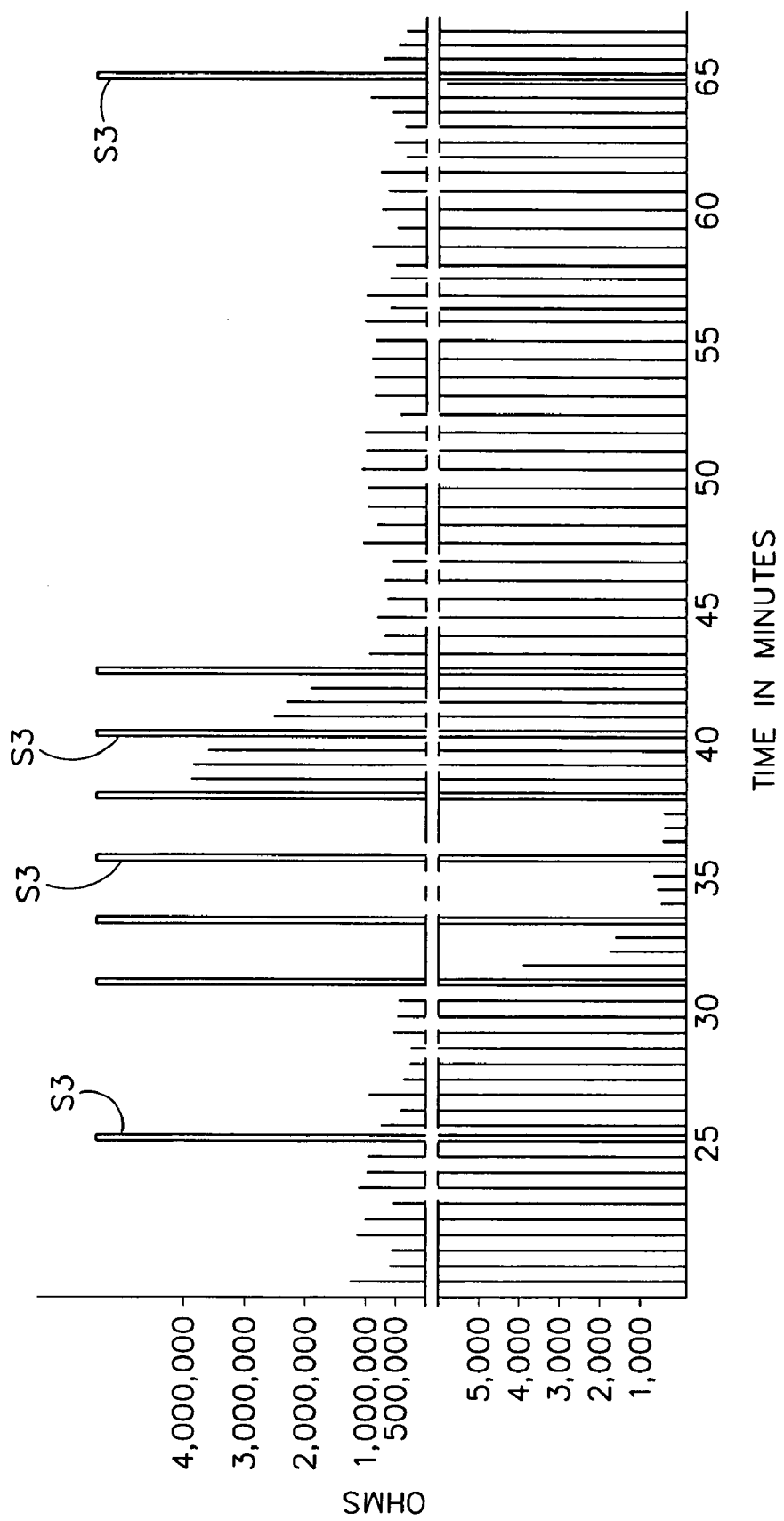
FIG. 13 is a chart showing the wetness measurement data gathered by the data collector every 35 seconds and transmitted via signals to the central computer system at 25 minute intervals when the sensor is clearly dry and at 140 second intervals when the sensor is damp or a potential wetness event is occurring.

The circuitry 200 also includes a wetness measurement circuit 255 that allows the data collector 100 to gather wetness measurement data corresponding to the actual wetness value of the sensor as shown in FIG. 13. The wetness measurement circuit 255 includes ports RC2 and RC3, contacts PC, PC2 and PC4, capacitor C3 and resister R2. The processor 220 is programmed to activate the wetness measurement circuit 255 and begin gathering wetness measurement data when a dry sensor 30 is properly secured to the data collector 100. The wetness measurement circuit 255 uses the same 3-volt potential applied to port RC3 used to generate the signal S1 for the sensor detection circuit. As shown in FIG. 11, a separate signal S2 branches off from signal S1 at PC4. Signal S2 travels from PC4 and down the length of conductive strip 62. Depending on the degree of wetness of the sensor 30, a portion of the signal S2 crosses from strip 62 to strip 61. The signal S2 then travels from strip 61 to contacts PC1 and PC2, and back to the processor 220 via port RC2. The return path takes the signal S2 by capacitor C3. The signal S2 is consumed by and will not pass capacitor C3 until the capacitor is charged to a predetermined level by the signal. Charging the capacitor C3 takes time and delays the receipt of the signal S2 at port RC2. The processor 220 uses its internal clock 227 to measure the time the signal S2 takes to charge capacitor C3 to its predetermined level and pass on to port RC2. The processor 220 looks for signal S2 at port RC2 about every 35 seconds (2.3 seconds×15).

When no sensor or a completely dry sensor 30 is attached to the data collector 100, capacitor C3 does not charge to its predetermined level because there is virtually an infinite resistance between the conductive strips 61 and 62, and no signal S2 will be received at port RC2. The processor 220 is programmed to configure this uncharged time measurement to correspond to a resistance of 4,200,000 ohms. When the sensor 30 is dampened or wetted by sweat, urine, tap water, or another dialectic material or fluid, the resistance between the conductive strips 61 and 62 decreases. This decrease in resistance allows a portion of the signal S2 to travel to and charge capacitor C3. The processor 220 measures the time between when the signal S2 is sent from port RC3 to the time the signal is received at port RC2. As noted above, the difference in time is the time the signal S2 takes to charge capacitor C3. The time measurements are correlated to resistance or wetness measurement data. FIG. 13 shows a continuous series of wetness measurement data obtained by the data collector 25 every 35 seconds.

The data compiling processor 220 compares each time or wetness measurement data to a predetermined power conservation value. In the preferred embodiment, this conservation value is set at 5,000 ohms, or the time it would take the signal S2 to charge capacitor C3 if a 5,000 ohm resistor were placed between the conductive strips 61 and 62. Test observations of the system 20 indicate that measurements of 5,000 ohms or above are indicative of a sensor 30 that is clearly dry to the touch, and measurements of about 3,000 ohms are indicative of a sensor that is just becoming noticeably damp to the touch. The processor 220 saves each resistance measurement in its memory 225. However, only the four most recent resistance measurement data are maintained in the memory 225. The older measurement data are written over or otherwise discarded. The wetness measurement circuit 255 determines the resistance of the sensor 30 to within 10% from 1,000 ohms to 1,000,000 ohms.

The data collection device 25 uses the transmitter 240 to periodically generate and transmit wetness measurement data signals S3 to the central computer 300, as shown in FIG. 13. The transmitter 240 preferably produces signals S3 having standard NRZ data, positive logic, one start bit, 8 data bits, and a stop bit. The data rate is preferably 9600 baud. The transmitter 240 is preferably an Inovonics serial transmitter model FA240XS. A unique identification number or code is programmed into each transmitter 240 and sent with each signal S3. The transmitter 240 is firmly secured to the lid 110 of the housing 102 as shown in FIG. 7.

The transmitter 240 sends signals S3 containing resistance or wetness measurement data whether the sensor 30 is dry, damp or wet as best shown in FIG. 13. To preserve power and the life expectancy of the battery 230 and data collector 100, wetness measurement data is sent less frequently or at a slower rate when the sensor 30 is relatively dry, and more frequently or a faster rate when the sensor is damp or wetted to a significant degree. When the resistance or wetness measurement data remains above the 5,000 ohm power conservation level, the processor 220 is programmed to measure resistance data about every 35 seconds and transmit data about every 25 minutes. Although about 50 measurements have been taken in this 25 minute period, only the four most recent resistance measurements remain in the memory 225 and are sent to the central computer 300. When the wetness measurement data falls below or otherwise exceeds the 5,000 ohm power conservation level, the processor 220 is programmed to continue measuring resistance data about every 35 seconds, but transmit that data about every 140 seconds (4×35). Each of the four wetness measurement data obtained by the data collector 100 and stored in its memory during this 140 second period are sent to the central computer 300, so that every resistance measurement indicative of a damp or significantly wet sensor 30 is sent to the central computer. As noted above, each signal S3 sent by the transmitter 240 includes the unique identification number for the transmitter 240, and thus the corresponding individual 5 wearing the device. Monitoring systems 20 for larger assisted living and nursing homes 10 utilize transceivers 260 located at convenient places about the assisted living or nursing home. These transceivers 260 receive and boost the signals S3 from the transmitters 240, and retransmit them to the central computer station 300.

The central computer station 300 is typically located at a central station or nursing station, as shown in FIGS. 1a and 1b. The control station 300 includes a processor 310, memory 312, monitor 315, printer 320, receiver 340 and base pager station 350. The control processor 310 is programmed with a password to limit access to authorized administrators and healthcare workers. The receiver 340 is compatible with the transmitter 240 for receiving signals S3, and is preferably an Inovonics serial receiver model FA403.

The base pager station or paging transmitter 350 is preferably an in house paging station such as the Scope Telepath 450. The control processor 310 and its accessories are backed up by an uninterruptible power supply.

The control processor 310 analyzes the wetness or resistance measurement data received by receiver 340 to determine whether or not a wetness event or a change event has occurred. The processor 310 is programmed with an adjustable wetness value or threshold level that is considered to be indicative of a wetness event. The programming allows an administrator at the nursing station to select this threshold level from one of several wetness sensitivity levels for each individual 5. A different sensitivity level can be selected for each individual 5 using the monitoring and detection system 20.

The processor 310 is programmed to allow the administrator or nurse to select either a "high," "medium" or "low" sensitivity level for each individual. The "high" sensitivity level will determine that a wetness event has occurred when the processor 310 receives five consecutive resistance measurements of 3,000 ohms or less. The "medium" or "medium" sensitivity level will determine that a wetness event has occurred when the processor 310 receives five consecutive resistance measurements of 2,000 ohms or less. The "low" sensitivity level will determine that a wetness event has occurred when the processor 310 receives five consecutive resistance measurements of 1,000 ohms or less. The "high" sensitivity level setting will cause the processor 310 to determine that a wetness event has occurred when the sensor 30 is slightly wet or has a low degree of wetness. The "middle" sensitivity level setting will cause the processor 310 to determine that a wetness event has occurred when the sensor 30 is mildly wet or has a middle degree of wetness. The "low" setting will only indicate a wetness event when the sensor is very wet or has a high degree of wetness. The computer system 300 will indicate that a wetness event has occurred when five consecutive resistance measurement data are received below the selected threshold or sensitivity level for a given individual. Although the system has been described to include three sensitivity levels, it should be understood that the system could have two sensitivity levels or an infinite number of sensitivity levels without departing from the broad aspects of the invention. Given that in the preferred embodiment each data signal S3 contains four wetness measurement data, which is fewer than the five consecutive wetness data measurements needed by the central computer system 300 to determine that a wetness event has occurred, at least two signals S3 are needed to determine that a wetness event has occurred.

The central computer system 300 has the capability to use a time derivative or rate of change factor of the wetness measurements to determine whether a wetness event has occurred. The processor 310 compares this rate of change measurement to a predetermined rate of change level to make this determination. The faster the rate of change in the wetness measurement data, the more likely a wetness event has occurred. The rate of change factor can be used by itself or together with the sensitivity threshold level information to determine whether a wetness event has occurred. This allows the processor 310 to use two different types of data to decide whether or not a wetness event has occurred.

When the central computer system 300 receives resistance or wetness measurement data from the data collector 100 of a particular individual 5 indicative of a wetness event for that individual (e.g., five consecutive resistance measurements below the selected sensitivity level for that individual), the control computer 310 time stamps the wetness measurement data as a wetness event and associates this wetness event with the particular individual 5 wearing the subject transmitter 240. The processor 310 displays the name or otherwise identifies the individual 5 having the wetness event on the monitor 315, and the time the wetness event was time stamped, as indicated in the monitor display 315 or report shown in FIG. 15. The monitor 315 or a report can also indicate the apartment or room number, or transmitter ID of the individual 5. The monitor 315 can also display other appropriate information, such as the name of the healthcare worker 7 assigned to the individual 5. The processor 310 may also sound an audible alarm at the nursing station.

The central computer system 300 then activates the base pager station 350 to send a page signal S4 to the pager 360 of an appropriate healthcare worker 7, as shown in FIGS. 1a and 1b. The page signal S4 contains a message or appropriate information to identify the individual in need of attention. For example, the page can indicate the individual's name, apartment or room number, transmitter ID, etc.

When the healthcare worker attends to the individual 5 and changes his or her wet garment 15 and sensor 30, the healthcare worker disconnects the wet or otherwise used sensor from the data collector 100. As discussed above, when the wet sensor 30 is removed, the data collector 100 determines that the wet sensor has been removed, but continues to gather and send infinite resistance measurement data to the central computer station 300 via signals S3, as indicated in FIG. 13. When a new sensor 30 is properly attached to the data collector 100, the sensor detection circuit detects its presence. The data collector 100 continues using its wetness measurement circuit to determine the resistance of the new sensor 30, and transmits the signal S3 with resistance data every 140 seconds for about four to five minutes. After this four to five minute interval has elapsed, the data collector 100 stops transmitting resistance data at the faster 140 second rate. Once the new sensor strip 30 is properly attached to the data collector 100, the programming of the data collector 100 instructs it to transmit signals S3 at the slower 25 minute rate. The first slower rate signal S3 is sent about 25 minutes after the sensor is properly attached to the data collector 100, provided the wetness measurement data remains above the power conservation level of 5,000 ohms. The data collector 100 continues sending resistance data every 25 minutes until the processor 220 measures a resistance below the power conservation level (5,000 ohms) as discussed above.

The data collector 100 can be taken out of service by simply removing the wet or dry sensor 30 from the data collector and not replacing it with another sensor. If the sensor 30 is wet when it is removed and not replaced, the data collector will stop sending resistance data to the central computer station 300 after four to five minutes. If the sensor 30 is dry when it is removed and not replaced, the data collector 100 will immediately stop sending resistance data.

The central computer system 300 considers a wet garment 15 changed when the resistance data received by the control computer 310 for a particular data collector 100 changes from a reading of below the power conservation level (5,000 ohms or less) to a reading of 50,000 ohms or greater. The computer 310 does not verify that the garment was changed until a signal S3 is received 25 minutes after the change event occurs. If no signal S3 is received at the 25 minute interval, the central computer 310 does not know whether a new garment was placed on the individual or whether the data collector 100 was simply taken out of service. When the central computer 310 determines that a garment change event has occurred, the computer time stamps this event, as shown in FIG. 15. The control computer 310 stores at least the wetness measurement date and transmitter ID, and approximate time of each wetness event and each change event in its memory 312 or an associated memory.

The central computer system 300 generates reports via its printer 320 based on transmitter ID, individual name or assigned healthcare worker name. The report scan take the form of a chart showing all the wetness measurement data obtained for a particular individual 5, as well as the time the data was received by the central computer station 300 as in FIG. 14. The reports can also take the form of a chart identify the approximate times of all the wetness events change events for one or move individuals 5, to ensure that each person is consistently receiving prompt attention by the healthcare workers 7, as in FIG. 15. The approximate duration of time between the wetness and change event for each person can also be noted or displayed.

The normal mode of operation for the data collector 100 has been described. However, it should be noted that the data collector 100 can be put into alternate modes during the set up, testing and servicing of the system 20. For example, an inferred transmission of encoded data can place the data collector 100 into a test mode where it sends resistance or wetness measurement data more frequently to aid in the manufacturing process and to demonstrate the system 20 and train the healthcare workers. The data collector 100 also has an internal counter that counts how many sensors 30 have been secured to the data collector. An inferred transmission of encoded data can instruct the data collector 100 to send this count to the central computer system 300. This count helps determine how much use the data collector 100 has had. An inferred transmission of encoded data can also be received by the data collector 100 to program a coded identification number into its wetness measuring circuit.

While the invention has been described with reference to a preferred embodiment, it will be understood by those skilled in the art that various changes may be made and equivalents may be substituted without departing from the broader aspects of the invention.

We claim:

1. A method of detecting wetness on an individual, said method of detecting wetness comprising the steps of:

providing a sensor formed by an absorbent material and spaced conductors, said conductors being spaced to produce an amount of resistance between said conductors, said absorbent material extending between said conductors and being adapted to absorb an amount of wetness, said amount of resistance between said conductors decreasing as said amount of wetness absorbed by said absorbent material increases, said sensor having an actual wetness value indicative of said amount of wetness absorbed by said absorbent material between said conductors, a data collector having a data compiling processor, electric circuit, communication device and power source, said circuit including said spaced conductors, and a control station having a receiver, control processor and associated memory containing a predetermined wetness value;

placing said sensor against the individual;

periodically obtaining wetness measurement data from said sensor at spaced intervals of time via said data collector, each of said wetness measurement data having a value indicative of said amount of wetness absorbed by said absorbent material at its corresponding interval of time;

periodically generating and transmitting said wetness measurement data from said data collector via said communication device to said control station via said receiver;

comparing each of said wetness measurement data with said predetermined wetness value;

determining that a wetness event has occurred when a predetermined number of said wetness measurement data exceed said predetermined wetness value; and, communicating that said wetness event has occurred via a communication device of said control station.

2. The method of detecting wetness of claim 1, and further including the step of storing said wetness measurement data in said associated computer of said control processor.

3. The method of detecting wetness of claim 1, and wherein said associated memory of said control processor has a second predetermined wetness value, and further including a step of determining that a change event has occurred when said control processor receives wetness measurement data above a second predetermined value subsequent to a wetness event.

4. The method of detecting wetness of claim 3, and wherein said control processor has an associated clock, and further including the steps of time stamping said wetness event, time stamping said change event, calculating a duration of time between said wetness and change events, and communicating said duration of time via said communication device of said control station.

5. The method of detecting wetness of claim 1, and wherein said data collector includes a data memory, and further including the step of storing each of said wetness measurement data in said data memory, each of said data signals containing a given number of said wetness measurement data stored in said data memory.

6. The method of detecting wetness of claim 5, and wherein said given number of wetness measurement data contained in one of said signals is fewer than said predetermined number of wetness measurement data needed to determine that a wetness event has occurred.

7. The method of detecting wetness of claim 1, and wherein said data collector has a data memory containing a predetermined power conservation value, and further including the step of comparing each of said wetness measurement data with said power conservation value, said data collector generating and transmitting said data signals at a first rate when said wetness measurement data is above said power conservation value, and at a second rate when one of said wetness measurement data falls below said power conservation value.

8. The method of detecting wetness of claim 1, and wherein said method of detecting wetness is for at least two different individuals, and further including a step of selecting said predetermined wetness value in said memory of said control processor from one of at least two sensitivity levels, a first sensitivity level being selected for one of the individuals and a second sensitivity level being selected for another of the individuals.

9. The method of detecting wetness of claim 1, and further including the steps of removably connecting said sensor to said data collector to obtain wetness measurement data, disconnecting said sensor from said data collector after a wetness event has occurred, cleaning said sensor, and removably connecting said cleaned sensor to said data collector to obtain wetness measurement data.

10. The method of detecting wetness of claim 1, and wherein said communication device of said control station includes a paging transmitter and a healthcare worker with a pager, and said step of communicating that said wetness event has occurred includes using said paging transmitter to send a page signal to said pager of the healthcare worker, said page signal containing a message indicating that the individual has had said wetness event.

11. The method of detecting wetness of claim 1, and wherein said step of placing said sensor against the individual requires said sensor to be placed directly against the individual.

* * * * *